US005834275A

United States Patent [19]

Raehse et al.

[11] Patent Number: 5,834,275
[45] Date of Patent: Nov. 10, 1998

[54] PROCESS FOR DEODORIZING FERMENTED CULTURE BROTHS WITH SUPERHEATED STEAM

[75] Inventors: Wilfried Raehse; Kathleen Paatz, both of Duesseldorf, Germany; Werner Pichler, Kundl, Austria; Horst Upadek, Ratingen, Germany

[73] Assignee: Henkel Kommanditgesellschaft auf Aktien, Duesseldorf, Germany

[21] Appl. No.: 750,657

[22] PCT Filed: Jun. 6, 1995

[86] PCT No.: PCT/EP95/02142

§ 371 Date: Jan. 17, 1997

§ 102(e) Date: Jan. 17, 1997

[87] PCT Pub. No.: WO95/34358

PCT Pub. Date: Dec. 21, 1995

[30] Foreign Application Priority Data

Jun. 15, 1994 [DE] Germany .......................... 44 20 730.1

[51] Int. Cl.[6] .............................. C12N 9/00; C12N 9/50; C12P 1/00; D06M 16/00

[52] U.S. Cl. ........................... 435/183; 435/41; 435/219; 435/264

[58] Field of Search .................................... 435/261, 243, 435/267, 183, 41, 219

[56] References Cited

U.S. PATENT DOCUMENTS

| | | | |
|---|---|---|---|
| 4,751,003 | 6/1988 | Raehse et al. | 210/639 |
| 5,352,604 | 10/1994 | Wilson et al. | 435/221 |
| 5,637,560 | 6/1997 | Raehge et al. | 510/443 |

FOREIGN PATENT DOCUMENTS

| | | |
|---|---|---|
| 0200032 | 11/1986 | European Pat. Off. . |
| 0554818 | 8/1993 | European Pat. Off. . |
| 2925427 | 1/1981 | Germany . |
| 4307115 | 9/1994 | Germany . |
| 4310506 A1 | 10/1994 | Germany . |
| 4322229 A1 | 1/1995 | Germany . |
| 1063393 | 3/1967 | United Kingdom . |
| WO9102792 | 3/1991 | WIPO . |
| WO9211347 A2 | 7/1992 | WIPO . |
| WO9316173 A1 | 8/1993 | WIPO . |
| WO9400563 | 2/1994 | WIPO . |
| WO9502031 | 1/1995 | WIPO . |

OTHER PUBLICATIONS

W. Raehse et al., "Mikrofiltration von Fermenterbruehen" (Microfiltration of Fermenter Broths), Chem. Ing. Techn. 57 (1985) No. 9, pp. 747–753, and the Primary Literature Cited Therein.

*Primary Examiner*—David M. Naff
*Attorney, Agent, or Firm*—Ernest G. Szoke; Wayne C. Jaeschke; Real J. Grandmaison

[57] ABSTRACT

A process is provided for deodorizing an aqueous culture broth composition by: (a) providing an aqueous culture broth composition containing odorous compounds in spray form; (b) providing a stream of superheated steam; (c) providing a spray zone in vacuo; (d) simultaneously introducing both the aqueous composition of (a) and the superheated steam into the spray zone causing the odorous compounds to be entrained in the superheated steam, thus forming a deodorized aqueous culture broth composition; (e) removing the superheated steam containing the entrained odorous compounds from the spray zone; and (f) discharging the deodorized aqueous culture broth composition from the spray zone. Preferably, the culture broth composition is maintained at a temperature of less than 50° C. in the spray zone to prevent inactivation of temperature-sensitive materials such as enzymes. Pressure in the spray zone may be about 10 to 250 mbar and temperature of the superheated steam can be up to 250° C. The superheated steam may be introduced into the spray zone countercurrent to the culture broth composition. The deodorized culture broth composition can be recycled to the spray zone for further deodorization.

9 Claims, No Drawings

PROCESS FOR DEODORIZING FERMENTED CULTURE BROTHS WITH SUPERHEATED STEAM

BACKGROUND OF THE INVENTION

1. Field of the Invention

The biotechnological production of useful materials and mixtures thereof by cultivation of selected microorganism populations is now of considerable industrial significance. The production of washing- and/or cleaning-active enzymes, more particularly from the classes of proteases, cellulases, lipases and amylases, and the production of pharmacologically active useful materials are mentioned purely by way of example in this regard. Aqueous preparations of intracellular and/or extracellular useful materials contaminated by a number of impurities, for example parts of the nutrient medium, accumulate as primary process products. Extensive prior art literature is available on the working up of such culture broths, cf. for example the article by W. Rähse et al. entitled "Mikrofiltration von Fermenterbrühen (Microfiltration of Fermenter Broths)" in Chem.-Ing.-Techn. 57 (1985), No. 9,747 to 753 and the primary literature cited therein. Examples of relevant patents include, for example, EP-B1 0 200 032, WO 93/16173 and earlier German patent applications DE 43 10 506 and DE 43 22 229.

2. Discussion of Related Art

The multistage working-up of these biotechnologically obtained aqueous culture solutions seeks in particular to remove unwanted constituents by optionally multistage filtration and/or by washing, generally followed by solidification of the aqueous preparation using solid carriers. In the bacteriological production of washing- and cleaning-active enzymes, which is of particular commercial relevance, a particular problem lies in the following situation: through the metabolism in the fermentation process, the biomass-containing fermenter broths contain small quantities of low molecular weight compounds, more particularly corresponding nitrogen compounds, which are distinguished by a highly obtrusive unpleasant odor and which can promote the degradation of the biotechnological useful materials to form other foul-smelling compounds. A typical example of these phenomena can be found in the biotechnological production of proteases or protease solutions which are intended for use in detergents, more particularly as a mixture component in laundry detergents. In addition to the prior art literature already mentioned, reference is also made in this regard to International patent application WO 91/2792. A biomass-containing fermenter broth containing around 70,000 protease units per gram (PU/g) is obtained using selected microorganisms (*Bacillus licheniformis*—ATCC 53926) by a process similar to the process described in German patent DE 29 25 427. In addition to dissolved proteases, salts, proteins and metabolism products, the fermenter broth also contains undissolved constituents, such as bacillus cells, residues of nutrient medium and mucilaginous substances. During the working-up of the fermenter broths (WO 92/11347), the proteases are stabilized and relatively coarse particles and undissolved constituents are removed by decantation or microfiltration. The protease solution is concentrated by ultrafiltration and subsequent evaporation in vacuo. The protease solution obtained is mixed with solid carrier materials and granulation aids and made up into enzyme granules for use in detergents.

Despite the elaborate purification and working-up processes, the concentrated protease solution still contains small quantities of low molecular weight nitrogen compounds with an unpleasant odor which can additionally accelerate degradation of the protease in storage to form other foul-smelling sulfur compounds, for example mercaptans or thioethers.

The problem addressed by the teaching according to the present invention was to remove these low molecular weight odorous compounds in an additional but simple step to such an extent that products of substantially neutral odor would be obtained, in particular after the usual encapsulation of the useful materials or mixtures thereof, self-initiated decomposition processes being ruled out or at least largely suppressed at the same time. The teaching according to the invention is disclosed in the following with reference to the production of correspondingly treated washing- and cleaning-active proteases from corresponding biotechnologically obtained fermenter broths. However, the teaching according to the invention is by no means confined to this particular example. The principles discussed in the description of the invention may be broadly applied to the field in question of useful materials and solutions thereof from biotechnological production and to related fields.

DESCRIPTION OF THE INVENTION

In a first embodiment, the present invention relates to a process for removing odorous compounds from liquid preparations of useful materials, more particularly in the recovery of useful materials from biologically obtained culture broths, characterized in that the liquid preparation is treated as a sprayed material with steam present as superheated steam under the working conditions of the spray zone.

The process according to the invention is particularly suitable for deodorizing and stabilizing aqueous preparations from the working-up of biotechnological culture broths, more particularly corresponding fermenter broths, the treatment of the sprayed liquid phase with the superheated steam in the sprayed zone preferably being carried out under reduced pressure. The choice of this process parameter of reduced pressure in the spray zone enables the maximum temperature of the material sprayed as droplets in the spray zone in contact with the superheated steam to be safely controlled in the manner described in detail in the following.

In another embodiment, the present invention relates to the use of the process for deodorizing liquid preparations of useful materials by treatment thereof with superheated steam in the spray zone for long-term stabilization of the activity of the useful materials and for removing the odorous substances from starting materials, more particularly water-containing starting materials, which contain dissolved and/or dispersed biotechnologically obtained useful materials.

PARTICULARS OF THE TEACHING ACCORDING TO THE INVENTION

Earlier hitherto unpublished International patent application PCT/EP 94/00563 describes an improved process for the distillation-based separation of multicomponent mixtures by steaming. In a first embodiment, the teaching of this earlier application relates to a process for intensifying and/or accelerating the distillation-based separation of multicomponent mixtures of at least partly organic origin by steaming with steam superheated at the working pressure to facilitate the removal of steam-volatile components of the starting material, the process being characterized in that a starting material which is liquid under the working conditions is steamed after spraying in the form of fine droplets, the starting material is sprayed by means of a propellent gas and superheated steam is used as the propellent gas.

A modified embodiment of this process according to the earlier patent application cited above is characterized in that an at least substantially water-free starting material which is liquid under the working conditions is sprayed into a stream of the superheated steam without using the propellent gas. Although this patent application mentions numerous fields of application and special examples of the application of this technology of deodorizing by steaming, it does not mention the field with which the invention is concerned, namely preparations of useful materials, more particularly water-containing preparations, from the field of biotechnological processes. The disclosure of the earlier application in question and the references therein to further prior art publications are hereby included as part of the disclosure of the present invention.

The principle of spraying the liquid preparation to be purified or deodorized using a propellent gas, namely superheated steam, as envisaged in this earlier application, may also be applied in the embodiment of the present invention presently under discussion. In a preferred embodiment of the invention, however, the liquid starting material is sprayed into a stream of the superheated steam without using a propellent gas. The teaching according to the invention is distinguished from the variant of the earlier application discussed in the foregoing by the fact that the material to be deodorized and/or stabilized is generally present in the form of an aqueous preparation of useful materials. Fermenter broths and other biotechnologically obtained primary products generally accumulate in the form of water-containing preparations with considerable water contents. Thus, the water content of the starting materials to be purified in accordance with the invention is generally at least 15% by weight and preferably at least 35 to 40% by weight. In the field of detergent enzymes, an aqueous phase containing useful materials which has a water content of at least about 50% by weight and, for example, of 60 to 80% by weight is generally obtained as the product of primary and secondary purification stages. Aqueous solutions containing extracellular detergent proteases, which have been purified by optionally multiple-stage filtration and concentrated by additional evaporation in vacuo, generally contain around 55 to 75% by weight of aqueous phase before subsequent mixing with carrier materials, more particularly solid carrier materials. These water-containing preparations of useful materials are the preferred starting material according to the invention for deodorization and stabilization by treatment with superheated steam in the spray zone. In the preferred embodiment, no propellent gas is used. The aqueous protease solution is treated, preferably in countercurrent, with superheated steam flowing through the spray zone under the process conditions described in detail in the following. This treatment may be carried out in one or more stages. A multistage treatment in the spray zone is generally preferred. This multistage treatment may be carried out by partial recycling of the aqueous phase into the spray zone, although it is also possible to arrange several spray zones one behind the other. These spray zones arranged in the form of a cascade may be operated under the same or different conditions. For the adequate deodorization and stabilization of aqueous protease solutions, a two- to five-stage treatment of the aqueous starting solution in the spray zone can lead to satisfactory purification.

Useful materials containing viable organisms or constituents thereof, such as enzymes or other products of biotechnological cultures, and mixtures of such useful materials are often highly sensitive to temperature. This applies in particular to detergent enzymes, for example proteases of the described type. The working-up of the biological material has to take this temperature sensitivity into consideration. This does of course also apply in particular to the treatment stage with superheated steam according to the present invention. The teaching according to the invention controls and satisfies this requirement very simply by predetermining and monitoring the maximum temperature of the material in the spray zone by establishing and regulating the pressure conditions therein. According to the invention, the spray zone is generally operated in vacuo. The vacuum specifically established in the spray zone determines the boiling temperature of the water. The water introduced in comparatively large quantities with the liquid starting material also performs the protective function of regulating temperature in the spray zone. The superheated steam, which is optionally introduced at temperatures of the spray zone considerably above that boiling point, cannot lead to unwanted heating of the droplets of material in the spray zone as long as an adequate concentration of liquid aqueous phase in the droplets is guaranteed. The thermal energy introduced with the superheated steam is collected by corresponding evaporation of part of the water without any significant increase in temperature in the droplets. The working conditions to be applied in accordance with the invention make use of this natural law. Preferred working conditions in the spray zone are those under which there is very little, if any, simultaneous concentration of the aqueous starting phase. This rule applies at least to highly temperature-sensitive useful materials such as detergent proteases.

If desired, however, the process as a whole may also be modified to the extent that comparatively highly diluted starting solutions of the biotechnological useful materials are delivered to the spray zone where they are not only deodorized, but also partly concentrated (cf. earlier application PCT/EP 94/00563).

For the purification and stabilization of detergent proteases in accordance with the invention, it can be useful to maintain material temperatures in the spray zone of at most about 45° to 50° C. and preferably in the range from at most about 35° to 40° C. In particularly preferred embodiments, material temperatures of at most about 30° C. are established in the spray zone, the working conditions and, in particular, the vacuum to be established in the spray zone often being adapted to maximum boiling temperatures of the water of about 20° to 25° C. The particular choice of the working pressure in the spray zone is determined by the natural dependence of the boiling point of the water upon the working pressure established. In practice, working pressures in the spray zone of about 10 to 250 mbar and preferably in the range from about 15 to 50 mbar can be useful.

The steam introduced into the spray zone for the purifying treatment may be used at temperatures considerably above the boiling temperature of water under the working conditions. Thus, the temperature of the steam introduced may be at least 50° C. and preferably at least 100° C. above the boiling temperature of water under the working pressure of the purifying stage. Temperatures at least 150° to 200° C. above the boiling temperature of water under the working pressure of the purifying stage can be suitable. Based on normal pressure, preferred temperatures for the steam according to the invention are up to 250° C. and preferably up to 200° C. temperatures of around 130° to 200° C. being particularly preferred.

In preferred embodiments, the water-containing starting material to be purified can be delivered to the spray zone at a temperature which corresponds at least substantially to the boiling temperature of water under the working conditions. However, the limiting factors arising out of the temperature sensitivity of the biological useful material will of course have to be taken into account in this regard. In practice, therefore, the temperature range for the liquid starting material to be delivered to the spray zone, for example in the purification of aqueous protease solutions, will generally be in the range from about 20° to 35° or 40° C.

Another feature of the aqueous enzyme solutions to be treated in accordance with the invention can also be of importance. Aqueous culture solutions of biotechnological useful materials are often distinguished by a certain thixotropic behavior. The flowability of the aqueous mixture of useful materials can be ensured by suitable auxiliary measures, more particularly by the introduction of shear forces into the material to be purified. More particularly, the design and construction of the spray zone should also ensure that the sprayed material can be reliably discharged. In overall terms, the establishment of the working conditions for spray purification in accordance with the invention can be co-determined by this effect, as known per se to the expert. Characteristic working parameters of relevance in this regard are given in the following process Example.

EXAMPLE

A biomass-containing fermenter broth with a content of around 70,000 protease units per gram (PU/g), prepared by fermentation of *Bacillus licheniformis* (ATCC 53926) by the process described in German patent DE 29 25 427, is distinguished by an undesirably strong odor. Besides dissolved proteases, salts, proteins and metabolism products, this fermenter broth also contains undissolved constituents, such as bacillus cells, residues of the nutrient medium and mucilaginous substances. The fermenter broth initially accumulating is first worked up in accordance with International patent application WO 92/1134, relatively coarse particles and undissolved constituents being removed by decantation or microfiltration. The protease solution thus prepurified is concentrated by ultrafiltration and subsequent evaporation in vacuo. The protease solution thus concentrated can be mixed with solid carrier materials and granulation aids and made up into enzyme granules for use in detergents.

The protease solution thus worked up and hence the enzyme granules are also distinguished by an unwanted odor. In addition, the low molecular weight nitrogen compounds responsible, which are present in small quantities, accelerate the protease degradation process which in turn leads to the formation of other foul-smelling sulfur compounds (for example mercaptans, thioethers).

To remove the odorous compounds, the aqueous protease solution is deodorized in the spray zone in an additional process step carried out in accordance with the invention after evaporation in vacuo. The following parameters are applied in this additional process step:

The aqueous enzyme solution has a dry matter content (enzymes+fermentation residues) of 35% and the following data at 25° C.: Density: 1,100 kg/m$^3$

TABLE 1

Viscosity of the Aqueous Enzyme Solution as a Function of the Shear Rate

| Shear Rate (S$^{-1}$) | Viscosity (mPas) |
|---|---|
| 32.5 | 160 |
| 54.3 | 116 |
| 106.0 | 81.8 |
| 150.9 | 69.8 |
| 252.3 | 57.0 |
| 420.3 | 50.0 |
| 701.3 | 43.5 |
| 1169.0 | 41.0 |

During the deodorizing treatment, the enzyme solution was sprayed into a tank from above. The enzyme solution collected at the bottom of the tank and was recycled to the spray nozzle. The superheated steam entered the deodorizing tank in uniform distribution in countercurrent to the liquid.

The steam and the odorous substances entrained were discharged through a vacuum system with condensation of the steam. The pressure in the tank was 20 mbar absolute. Table 2 shows the dimensions of the deodorizing tank and the nozzle and the operating parameters adjusted.

TABLE 2

Dimensions of the Deodorizing Tank and Operating Parameters for the Tests with Protease Solution

| Dimensions | |
|---|---|
| 1. Deodorizing tank: | |
| Diameter | 300 mm |
| Height | 1,200 mm |
| 2. Hollow cone nozzle | |
| Diameter | 0.6 mm |
| Mean volumetric droplet diameter | around 60 μm |
| Operating parameters | |
| Protease solution | |
| Throughflow | 10 kg/h |
| Pressure at nozzle | 10 bar |
| Temperature | 25° C. |
| Steam | |
| Throughflow | 1.7 kg/h |
| Pressure | 1 bar abs. |
| Temperature | 170° C. |

The protease solution was recycled through the deodorizing stage three times and then made up into enzyme granules as described above. The odor notes of the enzyme granules improved from 4.5–5 to 3 (evaluation under the school marking system of 1 to 5).

We claim:

1. A process for deodorizing an aqueous culture broth composition obtained by fermentation of a culture medium with a microorganism, said process comprising:
   (a) providing, in spray form, an aqueous culture broth composition containing odorous compounds;
   (b) providing a stream of superheated steam;
   (c) providing a spray zone under reduced pressure;
   (d) simultaneously introducing both the aqueous culture broth composition and the superheated steam into the spray zone while maintaining the temperature of said aqueous culture broth composition at a temperature of less than 50° C. resulting in the odorous compounds being entrained in the superheated steam, thus deodorizing the aqueous culture broth composition;

(e) removing the superheated steam containing the entrained odorous compounds from the spray zone; and (f) discharging the deodorized aqueous culture broth composition from the spray zone.

2. The process of claim 1 wherein the aqueous culture broth composition contains low molecular weight odorous compounds.

3. The process of claim 1 wherein the aqueous culture broth composition is an aqueous enzyme fermentation broth.

4. The process of claim 1 wherein the aqueous culture broth composition contains at least 15% by weight of water, based on the weight of the composition.

5. The process of claim 4 wherein the aqueous culture broth composition contains at least about 50% by weight of water, based on the weight of the composition.

6. The process of claim 1 wherein the spray zone is under a working pressure of from about 10 to 250 mbar.

7. The process of claim 1 wherein the superheated steam has a temperature of up to 250° C.

8. The process of claim 1 wherein the superheated steam is introduced into the spray zone in countercurrent to the aqueous culture broth composition.

9. The process of claim 1 further comprising recycling the deodorized aqueous culture broth composition back into the spray zone for further deodorization.

* * * * *